US012458736B2

(12) United States Patent
Tanaka et al.

(10) Patent No.: US 12,458,736 B2
(45) Date of Patent: Nov. 4, 2025

(54) ELECTRIC BREAST PUMP, METHOD OF CONTROLLING ELECTRIC BREAST PUMP, AND CONTROL PROGRAM FOR ELECTRIC BREAST PUMP

(71) Applicant: PIGEON CORPORATION, Tokyo (JP)

(72) Inventors: Yuichiro Tanaka, Tokyo (JP); Satoru Saito, Tokyo (JP); Sumiko Kuroishi, Tokyo (JP)

(73) Assignee: PIGEON CORPORATION, Tokyo (JP)

(*) Notice: Subject to any disclaimer, the term of this patent is extended or adjusted under 35 U.S.C. 154(b) by 904 days.

(21) Appl. No.: 16/972,749

(22) PCT Filed: Jun. 7, 2019

(86) PCT No.: PCT/JP2019/022785
§ 371 (c)(1),
(2) Date: Dec. 7, 2020

(87) PCT Pub. No.: WO2019/235626
PCT Pub. Date: Dec. 12, 2019

(65) Prior Publication Data

US 2021/0260261 A1 Aug. 26, 2021

(30) Foreign Application Priority Data

Jun. 8, 2018 (JP) ................................. 2018-110743

(51) Int. Cl.
*A61M 1/06* (2006.01)
*A61M 1/00* (2006.01)

(52) U.S. Cl.
CPC ............ *A61M 1/0693* (2021.05); *A61M 1/06* (2013.01); *A61M 1/0697* (2021.05);
(Continued)

(58) Field of Classification Search
CPC ...... A61M 1/06; A61M 1/069; A61M 1/0693; A61M 1/0697; A61M 1/06935
See application file for complete search history.

(56) References Cited

U.S. PATENT DOCUMENTS

| | | | | |
|---|---|---|---|---|
| 6,461,324 B1 * | 10/2002 | Schlensog | A61M 1/06 604/74 |
| 2008/0009815 A1 * | 1/2008 | Grabenkort | A61M 1/81 604/74 |
| 2011/0004154 A1 * | 1/2011 | Van Schijndel | A61M 1/732 604/74 |

FOREIGN PATENT DOCUMENTS

| | | |
|---|---|---|
| CN | 10903054 A | 12/2010 |
| JP | 5677749 B2 | 2/2015 |

OTHER PUBLICATIONS

Office Action of the corresponding CN application No. 201980037936.2 mailed Dec. 21, 2022 and English translation thereof.

* cited by examiner

*Primary Examiner* — Kevin C Sirmons
*Assistant Examiner* — Antarius S Daniel
(74) *Attorney, Agent, or Firm* — Muncy, Geissler, Olds & Lowe, P.C.

(57) ABSTRACT

An electric breast pump 1 includes a breast placement part 12 in which a breast part including a breast and a nipple of a subject is placed and suction-pressure generating units 10 and 50 that generate a suction pressure in the breast placement part. The suction-pressure generating unit generates a suction cycle including a plurality of sucking operations. The suction cycle includes basic suction and increased suction with an increased suction pressure. A suction pressure difference that increases in the increased suction is a pressure difference at a borderline at which a user perceives a change of a suction pressure. In the suction cycle, the basic
(Continued)

suction and the increased suction are each repeated multiple times consecutively at an equal suction pressure. At least a last sucking operation in the suction cycle is extended suction having a longer suction time than those of other sucking operations.

11 Claims, 3 Drawing Sheets

(52) U.S. Cl.
CPC ........... *A61M 1/06935* (2021.05); *A61M 1/74* (2021.05); *A61M 1/75* (2021.05); *A61M 1/82* (2021.05); *A61M 2205/33* (2013.01)

ELECTRIC BREAST PUMP, METHOD OF CONTROLLING ELECTRIC BREAST PUMP, AND CONTROL PROGRAM FOR ELECTRIC BREAST PUMP

TECHNICAL FIELD

The present invention relates to an electric breast pump used for pumping milk by, for instance, a mother, a method of controlling the electric breast pump, and a control program for the electric breast pump.

BACKGROUND ART

Conventionally, a breast pump is used when milk is pumped for, for example, a baby by a mother and is stored in a feeding bottle or the like.

Breast pumps include a so-called a "manual breast pump" and an "electric breast pump".

The "manual breast pump" has a lever that swivels in response to an operation by an operator. The lever swivels to generate a negative-pressure space in a main body of the breast pump.

By using the negative-pressure space, milk is drawn and pumped from a breast of a mother.

The "electric breast pump" is not provided with a lever to be operated by an operator, and the pump is driven by the force of a motor or the like, whereby a negative-pressure space is generated in the main body of the breast pump by the pump, and milk is drawn and pumped from a breast of a mother by using this negative-pressure space (for example, PTL 1).

Such an "electric breast pumps" is frequently used when mothers who are busy in childcare need to pump a large amount of milk in a short period of time. Thus, in order to pump a large amount of milk in a short time, the suction pressure of an electric breast pump has to be forcibly increased, resulting in extension of time for pumping milk.

Thus, a conventional electric breast pump is configured to allow, for instance, a mother who is a user of the breast pump, to freely adjust the intensity and speed of suction.

CITATION LIST

Patent Literature

[PTL 1] Japanese Patent No. 5677749

SUMMARY OF INVENTION

Technical Problem

However, in many cases, the users, e.g., mothers, of electric breast pumps do not know appropriate suction pressure. Thus, it is difficult for them to operate an electric breast pump at, for example, an appropriate suction pressure.

Hence, an object of the present invention is to provide an electric breast pump that allows a user, e.g., a mother, to pump milk at an appropriate suction pressure, a method of controlling the electric breast pump, and a control program for the electric breast pump.

Solution to Problem

According to the present invention, the object is attained by an electric breast pump including a breast placement part in which a breast part including a breast and a nipple of a subject is placed and a suction-pressure generating unit that generates a suction pressure in the breast placement part, wherein the suction-pressure generating unit generates a suction cycle including a plurality of sucking operations, the suction cycle includes basic suction and increased suction with an increased suction pressure, a suction pressure difference that increases in the increased suction is a pressure difference at a borderline at which a user perceives a change of a suction pressure, in the suction cycle the basic suction and the increased suction are each repeated multiple times consecutively at an equal suction pressure, and at least a last sucking operation in the suction cycle is extended suction having a longer suction time than those of other sucking operations.

With this configuration, the suction cycle generated by the suction-pressure generating unit includes the basic suction and the increased suction and suction pressures of the same kind are successively generated.

Moreover, an increase in suction pressure in the increased suction is a pressure difference at a borderline at which a user perceives a change of a suction pressure.

In other words, the suction cycle includes the increased suction, a change of the increase is a change at a borderline at which a user perceives a change of a suction pressure.

Thus, appropriate fluctuations in suction pressure can suppress pain at a nipple or areola mamma of a user while keeping the efficiency of milk pumping, thereby improving the comfort of use.

In this configuration, at least the last sucking operation in the suction cycle serves as extended suction having a longer suction time than those of other sucking operations.

Thus, the amount of pumped milk can be ensured by the extended suction.

Conventionally, suckling by a baby is considered to be ideal on the basis of consideration that suckling is not an artificial but natural action. Thus, conventional breast pumps have been designed to imitate the suckling by a baby.

However, it has been found that comfort for users, e.g., mothers, in the suction of a breast pump is not necessarily improved only by imitating the sucking action of a baby.

For example, if the pressure fluctuation pattern becomes inappropriate, the efficiency of milk pumping decreases and causes pain and discomfort to users, e.g., mothers, of the breast pump.

For this, in the suction cycle of the configuration, a pattern of "cyclical fluctuation" is implemented. In this case, "cyclical fluctuation" means a suction pattern in which elements of sucking by a baby are extracted and a suction pattern including the elements is regenerated without reducing an amount of pumped milk and without impairing the comfort of use.

In the configuration, the "cyclical fluctuation (Yuragi-Cycle)" stimulates the user with a constant rhythm and relaxes the body of a user.

The relaxing enhances parasympathetic activity and hormone secretion necessary for milk production and milk ejection.

Hence, with this configuration, an electric breast pump can be implemented in which the "suction cycle" that elicits the foregoing effect, and the like, can be automatically activated and users, e.g., mothers, can pump milk at an appropriate suction pressure.

The electric breast pump is preferably configured such that in the extended suction, an increase speed, at which a suction pressure reaches a maximum suction pressure, is changed in order to shorten a holding time of holding the maximum suction pressure while an amount of suction of milk is secured.

With this configuration, an increase speed (for example, a rising speed) at which a suction pressure reaches the maximum suction pressure is changed (for example, increased or reduced).

Thus, the time of peak hold for keeping a pressure can be shortened while a suction pressure reaches the maximum suction pressure, thereby minimizing a length of time a user feels pain.

In order to secure the amount of pumped milk, it is preferable to increase a suction pressure to the maximum suction pressure and keep the pressure in that state. In this configuration, however, the increase speed of a suction pressure is changed without being kept constant, so that the amount of suction of milk can be secured.

In the extended suction of the electric breast pump, the increase speed is preferably high at a start of suction and gradually decreases as a suction pressure approaches the maximum suction pressure.

With this configuration, the increase speed is high at a start of suction and gradually decreases as a suction pressure approaches the maximum suction pressure.

Thus, when the change is plotted on a graph or the like, the change appears like a gentle slope, securing the same amount of pumped milk as in a case where a pressure is linearly increased and the peak is held at a target pressure.

Moreover, the peak hold can be shortened, thereby minimizing a length of time a user feels pain.

An interval, at which a suction pressure is not generated, is preferably formed between the suction cycles of the electric breast pump, and a period of time of the interval is changed based on the increase speed in the extended suction of the cycle immediately before and/or immediately after the interval.

When the interval is short, for example, if the increase speed of the extended suction of the suction cycle is high immediately before and/or immediately after the interval, a certain rhythm as comfort for users is disrupted, an interval between suction cycles is felt to have been shortened, and a repetitive rhythm with a sense of being rushed is felt.

In the configuration, the time of the interval is changed based on the increase speed in the extended suction immediately before and/or immediately after the interval.

In other words, the time of the interval can be adjusted according to the increase speed. Thus, in the configuration above, a user can feel a rhythm of stable cycle repetition.

Moreover, the time length of the interval is adjusted so as to repeat the suction cycle with a certain rhythm, allowing a user to feel rhythmic comfort.

In the suction cycle of the electric breast pump, the basic suction and the increased suction are preferably each repeated twice, and then the extended suction is performed.

With this configuration, the basic suction and the increased suction are each performed twice consecutively.

In contrast to the configuration, if the basic suction and the increased suction are each generated one time, the effect of a gradual increase in suction pressure is weakened, making it difficult for users, e.g., mothers, to pump milk at an appropriate suction pressure.

Conversely, if the basic suction and the increased suction are each generated five times, a user may slightly feel "insufficient suction" at successive low pressures and feel "pain" at successive high pressures.

Here, if the basic suction and the increased suction each include two consecutive sucking operations, the electric breast pump can pump milk at an appropriate suction pressure for users, e.g., mothers without causing the foregoing problem.

With this configuration, the suction pressure difference of the electric breast pump is 2.5 kPa to 3.5 kPa. According to the present invention, the object is attained by a method of controlling an electric breast pump including a breast placement part in which a breast part including a breast and a nipple of a subject is placed and a suction-pressure generating unit that generates a suction pressure in the breast placement part, the method including: generating, by the suction-pressure generating unit, a suction cycle including basic suction and increased suction with a suction pressure difference that increases and is a pressure difference at a borderline at which a user perceives a change of a suction pressure; repeating, in the suction cycle, each of the basic suction and the increased suction multiple times consecutively at an equal suction pressure; and causing a last sucking operation of the suction cycle to include extended suction having a longer suction time than those of the other sucking operations.

According to the present invention, the object is attained by a control program for causing an electric breast pump including a breast placement part in which a breast part including a breast and a nipple of a subject is placed and a suction-pressure generating unit that generates a suction pressure in the breast placement part to execute: a function of generating a suction cycle including basic suction and increased suction with a suction pressure difference that increases and is a pressure difference at a borderline at which a user perceives a change of the suction pressure; a function of repeating each of the basic suction and the increased suction multiple times consecutively at an equal suction pressure in the suction cycle; and a function of generating, as a last sucking operation of the suction cycle, extended suction having a longer suction time than those of the other sucking operations.

Advantageous Effects of Invention

The present invention can advantageously provide an electric breast pump that allows users, e.g., mothers, to pumping milk with an appropriate suction pressure, a method of controlling the electric breast pump, and a control program for the electric breast pump.

DESCRIPTION OF EMBODIMENTS

A preferred embodiment of the present invention will be specifically described below with reference to the accompanying drawings.

The following embodiment is a preferred specific example of the present invention and thus is technically limited in preferred ways. The scope of the present invention is not limited to these modes unless the present invention is limited in the following description.

Figure 1:
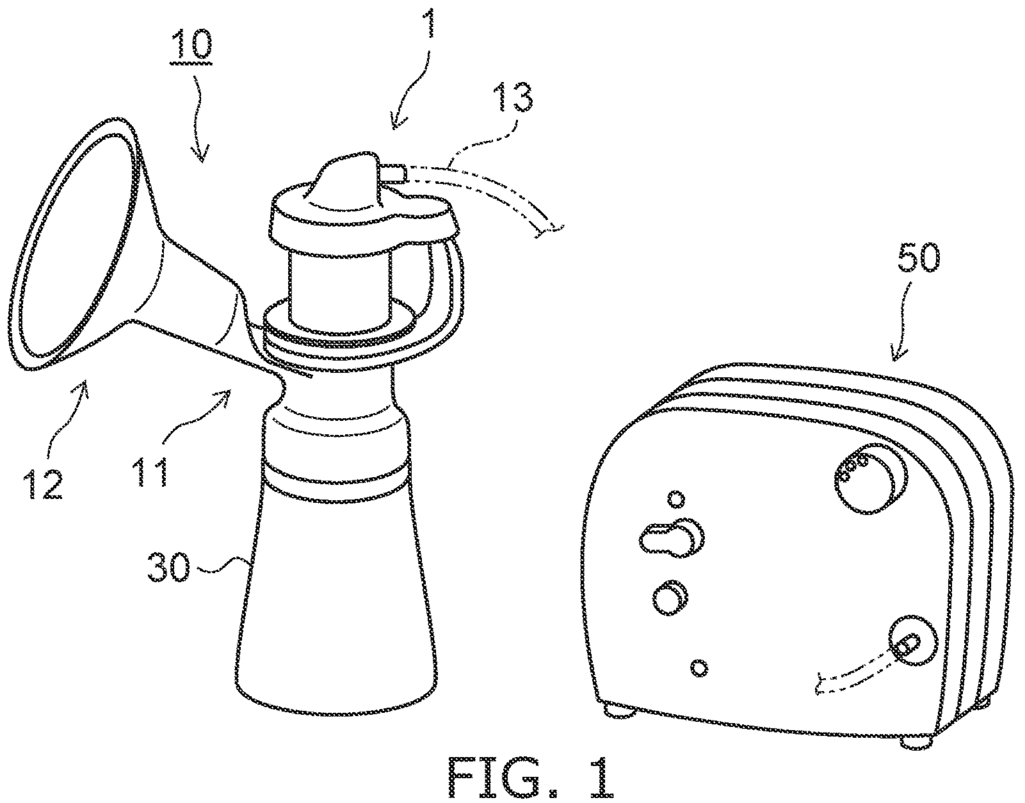
FIG. 1 is a schematic diagram illustrating the principal configuration of an electric breast pump according to the present invention.

FIG. 1 is a schematic diagram illustrating the principal configuration of an electric breast pump 1 according to the present invention.

As illustrated in FIG. 1, the electric breast pump 1 includes a breast pump 10 and a pump unit 50. The breast pump 10 and the pump unit 50 are connected to each other via a tube 13.

Moreover, as illustrated in FIG. 1, the breast pump 10 includes a breast-pump body 11, a bottle 30, and a breast placement part 12 in which a breast of a mother, who is a user of the electric breast pump 1, is placed.

Figure 2:
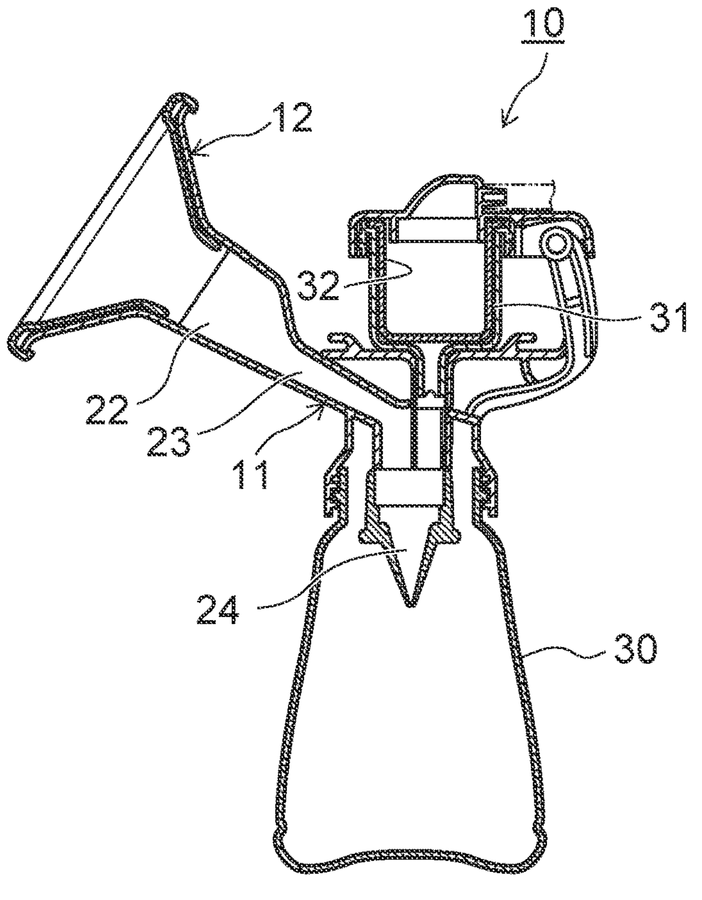
FIG. 2 is a schematic cross-sectional view illustrating the internal structure and the like of the breast pump.

FIG. 2 is a schematic cross-sectional view illustrating the internal structure of the breast pump 10.

As illustrated in FIG. 2, the breast pump 10 has a case 31. In the case 31, a deformable member 32 is disposed.

The pump unit 50 in FIG. 1 is started to rotate a motor provided in the pump unit 50, a negative pressure in the cylinder of the unit 50 changes, and the change is conveyed to the deformable member 32 via the tube 13, and an air pressure in the deformable member 32 decreases to deform the deformable member 32.

When the volume of the deformable member 32 considerably decreases in the case 31 as described above, an air pressure is largely reduced in an enclosed space 23 communicating with a space between the deformable member 32 and the case 31. Specifically, when a negative pressure increases in the enclosed space 23, milk is sucked from a breast placed in the breast placement part 12 of FIG. 2, and the pumped milk passes through an air passage 22 and is stored in the bottle 30 via a small chamber 24.

Thus, the breast-pump body 11 and the pump unit 50 or the like are examples of a suction-pressure generating unit for generating a suction pressure in the breast placement part 12.

(Operation Example of Electric Breast Pump 1)

In the following example, a mother pumps milk for a baby by using the electric breast pump 1 according to the present embodiment.

First, the mother to extract milk inserts her breast into the breast placement part 12 of the breast pump 10 in FIG. 1 and places her breast therein.

Subsequently, the switch of the pump unit 50 in FIG. 2 is operated to select a desired suction pressure.

As the suction pressure, a suction pressure of basic suction is selected in a range from, for example, −10 kPa to −31 kPa by a mother who is a user of the breast pump.

In the example of the present embodiment, a mother selects, for example, −10 kPa or −31 kPa as a suction pressure of the basic pressure.

Figure 3:
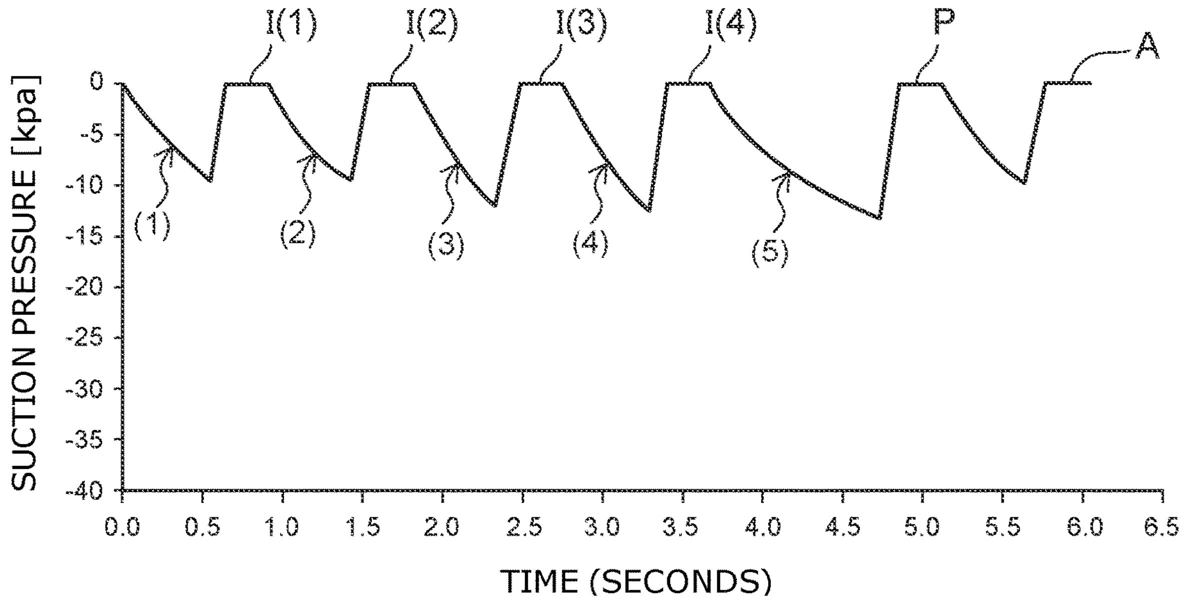
FIG. 3 is a schematic explanatory drawing indicating a suction cycle A of the electric breast pump when-10 kPa is selected as a suction pressure of basic suction.

FIG. 3 is a schematic explanatory drawing indicating a suction cycle A of the electric breast pump 1 when −10 kPa is selected as a suction pressure of the basic suction.

Figure 4:
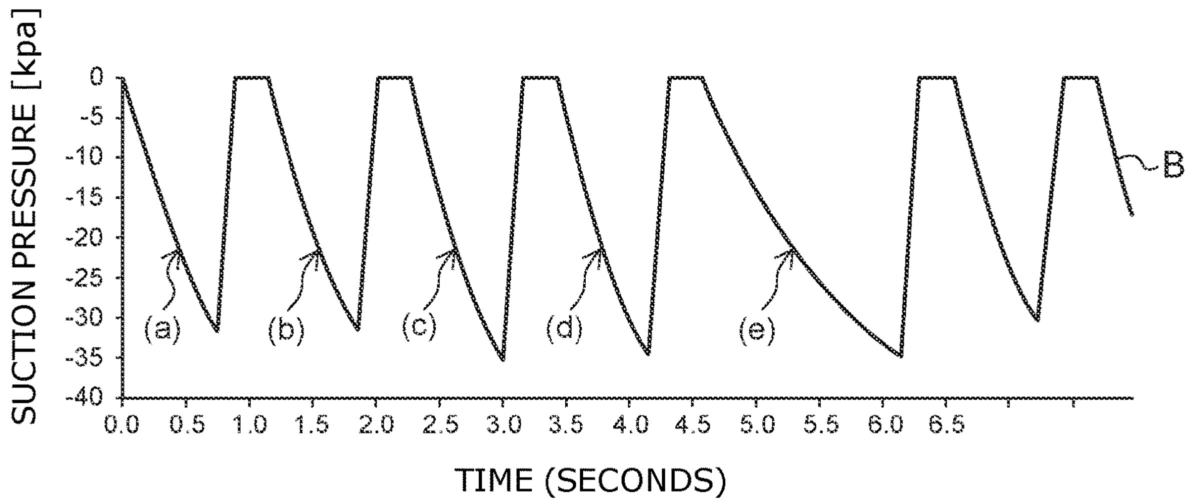
FIG. 4 is a schematic explanatory drawing indicating a suction cycle B of the electric breast pump when-31 kPa is selected as a suction pressure of the basic suction.

FIG. 4 is a schematic explanatory drawing indicating a suction cycle B of the electric breast pump 1 when −31 kPa is selected as a suction pressure of the basic suction.

In the suction cycle A of FIG. 3, for example, one cycle includes five sucking operations.

Specifically, the cycle includes “suction (1)” indicated by (1), “suction (2)” indicated by (2), “suction (3)” indicated by (3), “suction (4)” indicated by (4), and “suction (5)” indicated by (5) in FIG. 3.

As indicated in FIG. 3, a suction time is substantially kept constant from “suction (1)” to “suction (4)” but “suction (5)” is “extended suction” having a longer suction time than others as will be described later.

In this one cycle, a suction time in “suction (1)” to “suction (4)” is set at, for example, “0.75 seconds to 1.32 seconds”.

The suction time of “suction (5)” is set at, for example, 1.20 seconds to 2.10 seconds, which is longer than that of “suction (4)” preceding “suction (5)” by about 1.7 times to 1.9 times.

The suction cycle B in FIG. 4 includes five sucking operations starting from “suction (a)”. “Suction (a)” to “suction (e)” constitute one cycle.

“Extended suction”, a feature of the present embodiment, will be described below.

Figure 5:
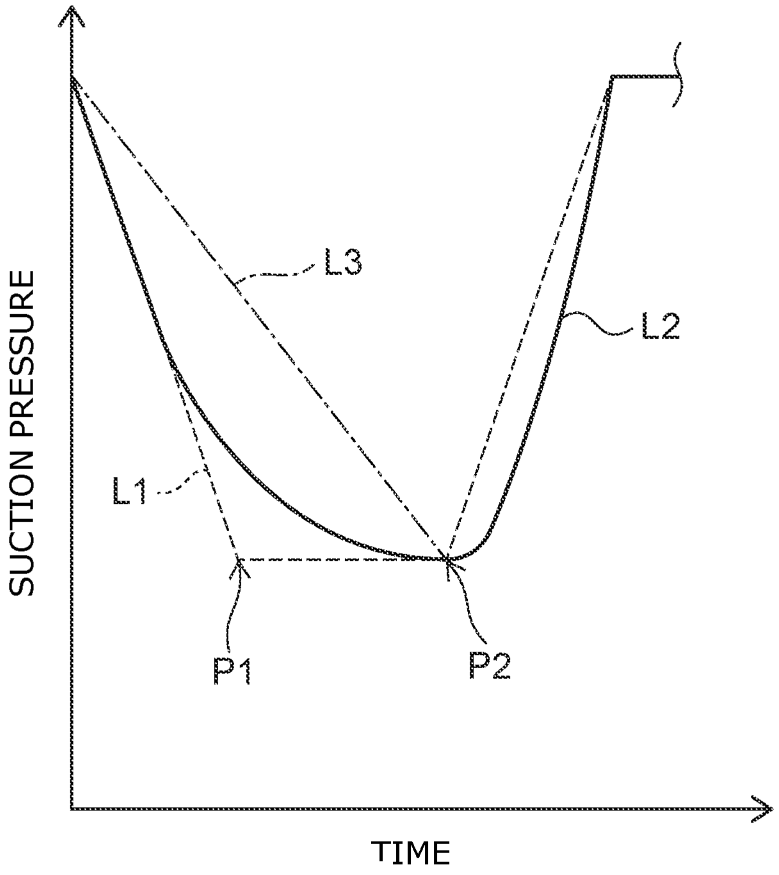
FIG. 5 is a schematic diagram indicating the specific contents of "extended suction" according to the present embodiment.

FIG. 5 is a schematic diagram indicating the specific contents of “extended suction” according to the present embodiment.

A broken line L1 in FIG. 5 indicates “peak hold” state in which so-called “rising speed” that is a pressure increase speed is kept constant from time P1 when “suction pressure” reaches a target pressure to time P2 when a pressure starts decreasing.

As described above, if the peak hold state in which a pressure is kept at the target pressure is extended, a nipple and the like of a subject, e.g., a mother can be sucked for an extended time, accordingly. This can obtain a large amount of pumped milk.

Unfortunately, in the extended peak hold state, a nipple and the like are sucked with a high pressure for a long time, so that a user may feel pain for a long time.

Hence, in the present embodiment, “rising speed” is not kept constant and an increase speed is changed. For example, at the start of suction, the increase speed is set “high” for a while and then is gradually set “low” as a pressure approaches a target pressure. Subsequently, a suction pressure is reduced immediately after the pressure reaches the target pressure.

In the present embodiment, this control enables “extended suction” in which “suction pressure” is plotted with “gentle slope” as indicated by a solid line L2 in FIG. 5.

The control of “suction pressure” can minimize the time of “peak hold” after the pressure reaches the target pressure.

This can minimize a time period during which a mother who uses the breast pump feels pain at her nipple and the like, so that the same amount of milk can be pumped as in the setting of extended peak hold indicated by the broken line L1 while pain felt by a mother is reduced.

A chain line L3 in FIG. 5 indicates a state in which “suction pressure” is increased with a constant increase speed in order to shorten the peak hold. In this case, the peak hold can be shortened but the amount of pumped milk cannot be secured.

Regarding this point, “extended suction” indicated by the solid line L2 of the present embodiment can reduce the pain of a user and secure the amount of pumped milk.

Furthermore, “extended suction” of “suction (5)” in FIG. 3 has a longer “suction time” than “suction (1)” to “suction (4)” preceding “suction (5)”. A combination with the normal suction provides comfortable “fluctuation (Yuragi)” for a user as will be described later.

However, if “rising speed” is “too low” at the suction start of “extended suction” of “suction (5)”, a mother who is using the breast pump may feel a rapid reduction in suction speed and feel the pump stopping.

Regarding this point, as described in the present embodiment, the rate of "rising speed" is "high" at the suction start of "extended suction", allowing a user to feel a change of suction as "fluctuation (Yuragi)".

The suction cycle in the example of FIG. 3 will be described below.

At the start of an operation of the electric breast pump 1, first suction is started. Subsequently, "suction (1)" as basic suction is performed.

"Suction (1)" has a suction pressure of −10 kPa.

Moreover, the suction time of "suction (1)" is, for example, about 0.7 seconds. The suction time is set constant at least at the same suction pressure.

After the suction, intervals having no generated suction pressures are provided. The intervals are all set at an equal time, for example, 0.15 seconds to 0.25 seconds.

After "suction (1)", an interval "I(1)" is provided and then "suction (2)" having the same suction pressure (−10 kPa) as "suction (1)" is performed.

Subsequently, "suction (3)" as increased suction is performed through an interval "I(2)".

The suction pressure of "suction (3)" is, for example, −13 kPa that is higher than the suction pressures (−10 kPa) of "suction (1)" and "suction (2)" by 3 kPa.

The increase in suction pressure may vary from 2.5 kPa to 3.5 kPa but is preferably set at 3 kPa.

"2.5 kPa to 3.5 kPa" is "pressure difference at a borderline at which a user perceives a change of a suction pressure".

The increase in suction pressure is set at "3 kPa" for the following reason.

The pressure increase of "3 kPa" is the borderline of a change of comfort for a mother who uses the electric breast pump 1. If the pressure difference is larger than 3 kPa, for example, the pressure difference is set at 6 kPa, a mother may feel pain and may feel insufficient suction at a low pressure.

In other words, because of an extremely large difference between a low pressure and a high pressure, a mother may feel that a low pressure is too low relative to a high pressure and may feel that a high pressure causes pain relative to a low pressure, leading to difficulty in adjustment to an appropriate pressure.

In the case of a suction pressure increase smaller than 3 kPa, for example, a pressure increase of about 2 kPa, a mother may hardly feel a pressure and thus feel "insufficient suction". This is not because "a pressure is hardly felt" but because a change of pressure is hardly felt. "Insufficient suction" results from the absence of perception of "fluctuation (Yuragi)".

After that, "suction (4)" is performed through an interval "I(3)" at the same suction pressure as "suction (3)".

Subsequently, "suction (5)" as "extended suction" is performed through an interval "I(4)".

The suction pressure of "suction (5)" is equal to the suction pressures (−13 kPa) of "suction (3)" and "suction (4)" serving as increased suction but the suction time of "suction (5)" is about 1.7 times to 1.9 times longer than those of increased "suction (3)" and "suction (4)".

The suction cycle of "suction (1)" to "suction (5)" provides appropriate fluctuations in pressure for a mother who uses the breast pump. This ensures "comfort" for a user and induces milk ejection relax. Thus, milk can be smoothly pumped.

An equal suction pressure is performed several times consecutively for the following reason.

If each suction pressure is increased to make a pressure difference, the suction pressure is not gradually increased but is rapidly increased. This may discomfort a mother.

However, if an equal suction pressure is repeated at least five times and then the pressure is increased, a mother may feel "insufficient suction" in a monotonous cycle having no fluctuations in pressure.

Thus, in the present embodiment, an equal suction pressure is generated twice consecutively and then the suction pressure is changed by 3 kPa.

In this way, one cycle of the suction cycle A is completed and then the same suction cycle A is started.

At this point, the subsequent suction cycle A is started through, for example, a pose P that is an interval indicated in FIG. 3.

The pose P is a part where a suction pressure is not applied and a sucking operation is not performed.

The pose P is provided between the cycles of "pressure-fluctuation suction pattern A" and the length of the pose P is changed according to, for example, "rising speed" that is the increase speed of "extended suction" of the cycle immediately before and/or immediately after the pose P, for example, "fifth suction (5)" in FIG. 3.

For example, when "rising speed" is high, the length of the pose P is increased, whereas when "rising speed" is low, the length of the pose P is reduced.

The length of the pose P is changed for the following reason.

For example, if high "rising speed" continues during the pose P in the short time, a certain rhythm as comfort for users is disrupted, an interval between suction cycles is shortened, and a repetitive rhythm with a sense of being rushed is felt.

In the present embodiment, the length of the pose P is adjusted according to "rising speed", allowing a user to feel a rhythm of stable cycle repetition.

Moreover, the length of the pose P is adjusted so as to repeat the suction cycle with a certain rhythm, allowing a user to feel rhythmic comfort.

In the present embodiment, the pose P and the intervals I(1) to (4) are provided so as to alternatively generate a time when a suction pressure is generated and a time when a suction pressure is not generated. This allows a user to pump milk with an appropriate rhythm.

As described above, one cycle of the suction cycle A in FIG. 3 is performed and is repeated a required number of times, allowing users, e.g., mothers, to pump milk.

Hence, the present embodiment can obtain the following effects.

In the present embodiment, a suction pressure is gradually increased by 3 kPa to a maximum pressure without a rapid increase. Thus, the nipples and areola mammae of users, e.g., mothers, are not rapidly stretched and the burden can be reduced.

Furthermore, for example, a suction cycle with an appropriate differential pressure of 3 kPa is a "cyclical fluctuation" for providing "fluctuation (Yuragi)" for a mother, preventing uncomfortable use by a mother.

In the present embodiment, suction fluctuates and a monotonous rhythm is not provided. Thus, the suction of the suction cycle is an appropriate "cyclical fluctuation", thereby providing comfortable feeling for a mother.

A mother can feel a rhythm of inhalation and rest, thereby comfortably pumping milk in a relaxed state.

Moreover, for a mother who frequently uses the electric breast pump 1 for pumping milk several times for a long time every day, the present embodiment can reduce an excessive long-time stretch of a nipple and prevent swelling of a nipple.

Even if a mother is a beginner of the electric breast pump 1 and is not used to stretching a nipple with suction, the present embodiment allows the mother to become used to a suction pressure of milk pumping as gentle suction.

Conventionally, suckling of a baby is regarded as being ideal because suckling is a natural action and is not artificial. Thus, conventional breast pumps have been intended to imitate suckling of a baby.

However, it is understood that comfort for users, e.g., mothers, is not always improved as the suction of an electric breast pump only by imitating the suction of a baby.

If the suction pattern becomes inappropriate, the efficiency of milk pumping decreases and causes pain and discomfort to a mother who uses the breast pump.

Regarding this point, the suction pattern A achieves a pattern of "fluctuation (Yuragi)". In this case, "fluctuation (Yuragi)" means a suction pattern in which the elements of suckling of a baby are extracted and a suction pattern including the elements is regenerated without reducing an amount of pumped milk and the comfort of use.

As described above, in the present embodiment, "cyclical fluctuation" stimulates a mother with a certain rhythm and relaxes the body of a user.

Moreover, the relaxing increases parasympathetic activity and enhances hormone secretion necessary for milk production and milk ejection.

Furthermore, in the present embodiment, one cycle includes "extended suction" like "suction (5)" in FIG. 3, so that as described above, a user hardly feels pain and a sufficient amount of pumped milk can be obtained.

Thus, the electric breast pump 1 can automatically operate the suction cycle that obtains the foregoing effect and pump milk with an appropriate suction pressure for users, e.g., mothers.

The suction cycle Bin FIG. 4 is substantially identical to the suction cycle A except for a suction time and a suction pressure starting from −31 kPa in the basic suction.

In the present embodiment, as illustrated in FIGS. 3 and 4, the basic suction is performed twice consecutively, increased suction with a pressure increased by 3 kPa is performed twice consecutively, and then the extended suction is performed one time. The present invention is not limited to this cycle and "extended suction" may be performed twice consecutively.

The present invention is not limited to this cycle and other suction cycles may be used as follows.

1) Suction Cycle of Three Consecutive Times

In the suction cycle, unlike in the embodiment, the basic suction is performed three times consecutively and then increased suction with an increased pressure is performed three times.

Thereafter, "extended suction" is performed one time to three times.

2) Suction Cycle of Twice and Three Times

In the suction cycle, unlike in the embodiment, the basic suction is performed twice, increased suction with an increased pressure is performed three times, and then extended suction is performed one time to three times.

3) Suction Cycle Including Second Increased Suction

In the suction cycle, unlike in the embodiment, the basic suction is performed twice, first increased suction with an increased pressure is performed twice, and then second increased suction increased by three pressures is performed twice, and then extended suction is performed one time to three times.

In the present embodiment, the present invention is implemented as, but is not limited to, an apparatus. The present invention may be a program executable by a computer and may be distributed while being stored in storage media including a magnetic disk (e.g., a floppy (registered trademark) disk or a hard disk), an optical disk (CD-ROM or DVD), a magneto-optical disk (MO), and semiconductor memory.

Any storage medium capable of storing programs and readable by a computer may be used. The storage format of the storage medium is not particularly limited.

Furthermore, processing for implementing the present embodiment may be partially performed by an OS (operating system) that operates on a computer in response to an instruction of a program installed on the computer from a storage medium and MW (middleware) including database management software and network software.

Moreover, the storage medium in the present invention is not limited to a medium independent of a computer. A storage medium for storage or temporary storage of a program transmitted and downloaded through a LAN or the Internet may be used.

The computer in the present invention may be any computer that performs processing in the present embodiment based on a program stored in a storage medium. An apparatus including a personal computer or a system including multiple apparatuses connected via a network may be used.

Alternatively, the computer in the present invention is not limited to a personal computer. The present invention also includes an arithmetic processing unit included in an information processor, and a microcomputer. A computer is a general name of equipment or an apparatus that can implement the functions of the present invention by means of programs.

In the foregoing explanation, the embodiment of the present invention was described. However, the present invention is not limited to the embodiment and can be changed in various ways within the scope of the claims. The configuration of the embodiment may be partially omitted or optionally combined with a different configuration.

REFERENCE SIGNS LIST

1 Electric breast pump
10 Breast pump
11 Breast-pump body
12 Breast placement part
13 Tube
222 Air passage
23 Enclosed space
24 Small chamber
30 Bottle
31 Case
32 Deformable member
50 Pump unit

The invention claimed is:

1. A method of controlling an electric breast pump including a breast placement part configured to be placed on a breast and a nipple of a subject is placed, and a suction-pressure generating unit configured to generate a suction pressure in the breast placement part, the method comprising:

generating by the suction-pressure generating unit a suction cycle including a plurality of suction operations, wherein the suction operations includes a plurality of basic suction operations having a basic suction pressure, a plurality of increased suction operations having an increased suction pressure that is greater than the basic suction pressure, and an extended suction operation having an extended suction pressure that is the same as the increased suction pressure of the increased suction operation and having 1.7 to 1.9 times longer suction time than that of the basic suction operations and the increased suction operations, and a suction pressure difference that is determined between a maximum suction pressure of the basic suction pressure and a maximum suction pressure of the increased suction pressure is ranged from 2.5 kPa to 3.5 kPa, wherein in the suction cycle, the basic suction operations and the increased suction operations are repeated multiple times consecutively at an equal suction pressure wherein the basic suction operations all have the same amount of the basic suction pressure, and the increased suction operations all have the same amount of the increased suction pressure, the basic suction operations are executed first, the increased suction operations are executed next, and the extended suction operation is executed at the same suction pressure as the suction pressure of the increased suction operation last such that there is no suction operation having a suction pressure that is smaller than that of a previous suction operation, and the suction cycle ends when the extended suction operation ends, and at the start of the extended suction operations, an increase speed of the suction pressure of the extended suction operation is set high, then is gradually reduced to low as the suction pressure approaches the maximum suction pressure, and then the suction pressure is reduced after the suction pressure reach the maximum suction pressure.

2. The method of controlling the electric breast pump according to claim 1, wherein in the extended suction operation, the increase speed, at which the suction pressure reaches the maximum suction pressure, is changed in order to shorten a holding time of holding the maximum suction pressure while an amount of suction of milk is secured.

3. The method of controlling the electric breast pump according to claim 2, wherein in the extended suction operation, the increase speed is high at a start of suction and gradually decreases as the suction pressure approaches the maximum suction pressure.

4. The method of controlling the electric breast pump according to claim 3, wherein an interval, at which a suction pressure is not generated, is formed between the suction cycles, and a period of time of the interval is changed based on the increase speed in the extended suction operation of the cycle immediately before and/or immediately after the interval.

5. The method of controlling the electric breast pump according to claim 4, wherein in the suction cycle, the basic suction operations and the increased suction operations are each repeated twice, and then the extended suction operation is performed.

6. The method of controlling the electric breast pump according to claim 3, wherein in the suction cycle, the basic suction operations and the increased suction operations are each repeated twice, and then the extended suction operation is performed.

7. The method of controlling the electric breast pump according to claim 2, wherein an interval, at which a suction pressure is not generated, is formed between the suction cycles, and a period of time of the interval is changed based on the increase speed in the extended suction operation of the cycle immediately before and/or immediately after the interval.

8. The method of controlling the electric breast pump according to claim 7, wherein in the suction cycle, the basic suction operations and the increased suction operations are each repeated twice, and then the extended suction operation is performed.

9. The method of controlling the electric breast pump according to claim 2, wherein in the suction cycle, the basic suction operations and the increased suction operations are each repeated twice, and then the extended suction operation is performed.

10. The method of controlling the electric breast pump according to claim 1, wherein in the suction cycle, the basic suction operation and increased suction operation are each repeated twice, and then the extended suction operation is performed.

11. A non-volatile memory storing a control program for causing an electric breast pump including a breast placement part configured to be placed on a breast and a nipple of a subject and a suction-pressure generating unit configured to generate a suction pressure in the breast placement part to execute:

a function of generating a suction cycle including a plurality of suction operations, wherein the suction operations includes a plurality of basic suction operations having a basic suction pressure, a plurality of increased suction operations having an increased suction pressure that is greater than the basic suction pressure, and an extended suction operation having an extended suction pressure that is the same as the increased suction pressure of the increased suction operation and having 1.7 to 1.9 times longer suction time than that of the basic suction operations and the increased suction operations, and a suction pressure difference that is determined between a maximum suction pressure of the basic suction pressure and a maximum suction pressure of the increased suction pressure is ranged from 2.5 kPa to 3.5 kPa, wherein the basic suction operations and the increased suction operations are repeated multiple times consecutively at an equal suction pressure in the suction cycle wherein the basic suction operations all have the same amount of the basic suction pressure, and the increased suction operations all have the same amount of the increased suction pressure, the basic suction operations are executed first, the increased suction operations are executed next, and the extended suction operation is executed at the same suction pressure as the suction pressure of the increased suction operation last such that there is no suction operation having a suction pressure that is smaller than that of a previous suction operation, and the suction cycle ends when the extended suction operation ends, at the start of the basic suction operations, an increase speed of the suction pressure of the basic suction operation is set high, then is gradually reduced to low as the suction pressure approaches the maximum suction pressure of the basic suction pressure, and then the suction pressure is reduced after the suction pressure reaches the maximum suction pressure of the basic suction pressure, and at the start of the increased suction operations, an increase speed of the suction pressure of the increased suction operation is set high, then is gradually reduced to low as the suction pressure approaches the maximum suction pressure of the increased suction pressure, and then the suction pressure is reduced after the suction pressure reaches the maximum suction pressure of the increased suction pressure.

* * * * *